US00PP17076P2

(12) United States Plant Patent
Danziger

(10) Patent No.: US PP17,076 P2
(45) Date of Patent: Sep. 5, 2006

(54) ***SOLIDAGO* PLANT NAMED 'DANSOLWIND'**

(50) Latin Name: ***Solidago* sp.**
Varietal Denomination: Dansolwind

(75) Inventor: Gabriel Danziger, Moshav Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 0 days.

(21) Appl. No.: 11/068,871

(22) Filed: Mar. 2, 2005

(51) Int. Cl.
*A01H 5/00* (2006.01)

(52) U.S. Cl. ..... Plt./263
(58) Field of Classification Search ..... Plt./263
See application file for complete search history.

*Primary Examiner*—Anne Marie Grunberg
*Assistant Examiner*—Georgia Helmer
(74) *Attorney, Agent, or Firm*—Foley & Lardner, LLP

(57) ABSTRACT

A new and distinct *Solidago* plant named 'Dansolwind' particularly characterized by having a plant height of 70–75 cm., small yellow inflorescences, green leaves, a rapid growth cycle and an even growth rate.

2 Drawing Sheets

Botanical description: *Solidago* sp.
Variety denomination: 'Dansolwind'.

BACKGROUND OF THE INVENTION

The present invention relates to a new and distinct cultivar of the goldenrod plant, botanically known as *Solidago* sp., and hereinafter referred to by the cultivar name 'Dansolwind'.

*Solidago,* of the sunflower family, *Asteraceae,* consists of approximately 100 species of goldenrod plants found in North America, most of which are geographically located in the East. Goldenrods are perennial plants that commonly grow along stream banks, ditches, roadsides and other areas where the soil is moist and rich.

The new *Solidago* cultivar is a product of a planned breeding program conducted by the inventor, Gabriel Danziger, in Moshav Mishmar Hashiva, Israel. The objective of the breeding program was to develop a new *Solidago* variety with a small yellow inflorescence, green leaves, a rapid growth cycle, and an even growth rate.

The new *Solidago* cultivar originated from a cross made by a planned breeding program discovered by the inventor in 2000 in Moshav Mishmar Hashiva, Israel. The female parent is designated as '1-Y-1' (unpatented). The male parent is unknown. The new *Solidago* cultivar 'Dansolwind' was selected by the inventor as a flowering plant within the progeny of the stated cross in a controlled environment in Moshav Mishmar Hashiva, Israel.

Asexual reproduction of the new *Solidago* cultivar by leaf cuttings was first performed in October, 2001, in Moshav Mishmar Hashiva, Israel, and has demonstrated that the combination of characteristics as herein disclosed for the new *Solidago* cultivar are firmly fixed and retained through successive generations of asexual reproduction. The new cultivar reproduces true to type.

BRIEF DESCRIPTION OF THE INVENTION

The following traits have been repeatedly observed and are determined to be unique characteristics of 'Dansolwind' which in combination distinguish this *Solidago* as a new and distinct cultivar:

1. Small yellow inflorescences;
2. 70–75 cm in height;
3. Green leaves;
4. Rapid growth cycle; and
5. Even growth pace.

Plants of 'Dansolwind' differ from the plants of the female parent, '1-Y-1' (unpatented) primarily in branch and inflorescence strength. 'Dansolwind' has sturdier branches and denser inflorescences than the mother plant.

Of the many commercial cultivars known to the present inventor, the most similar in comparison to 'Dansolwind' is the *Solidago* cultivar 'Tara' (unpatented). Both cultivars have small yellow inflorescences. However, the inflorescences of 'Tara' are a lighter yellow color, most similar to yellow group, RHS 7A, whereas the inflorescences of 'Dansolwind' are most similar to yellow group, RHS 13A.

BRIEF DESCRIPTION OF THE DRAWINGS/ PHOTOGRAPHS

The accompanying photographs illustrate the overall appearance of the new *Solidago* cultivar 'Dansolwind' showing the colors as true as is reasonably possible with colored reproductions of this type. Color in the photographs may differ slightly from the color value cited in the detailed botanical description which accurately describe the color of 'Dansolwind'.

DETAILED BOTANICAL DESCRIPTION

Figure 1:
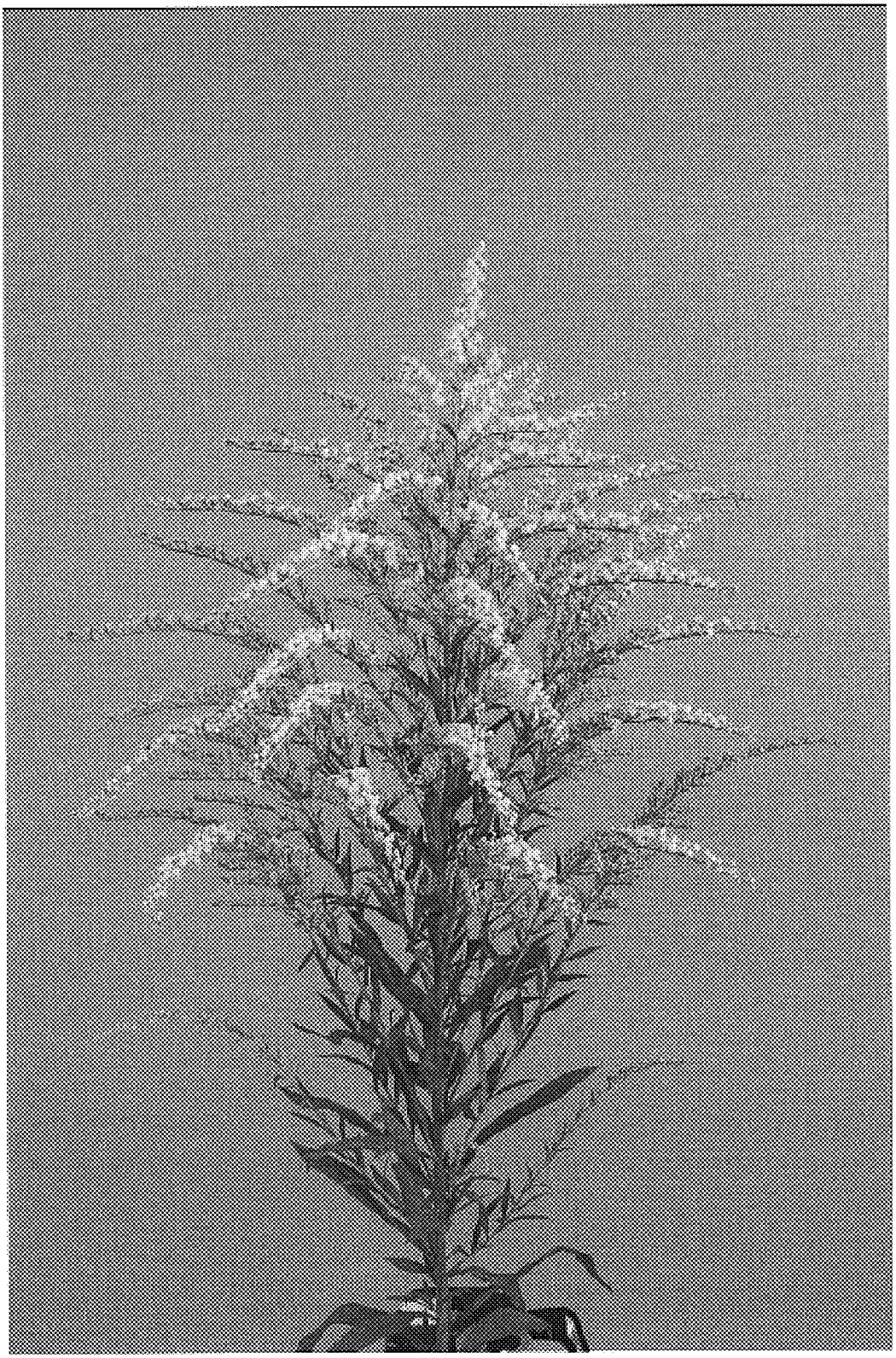
FIG. 1 shows a side view perspective of a typical, potted 'Dansolwind' at the age of 10 weeks.
Figure 2:
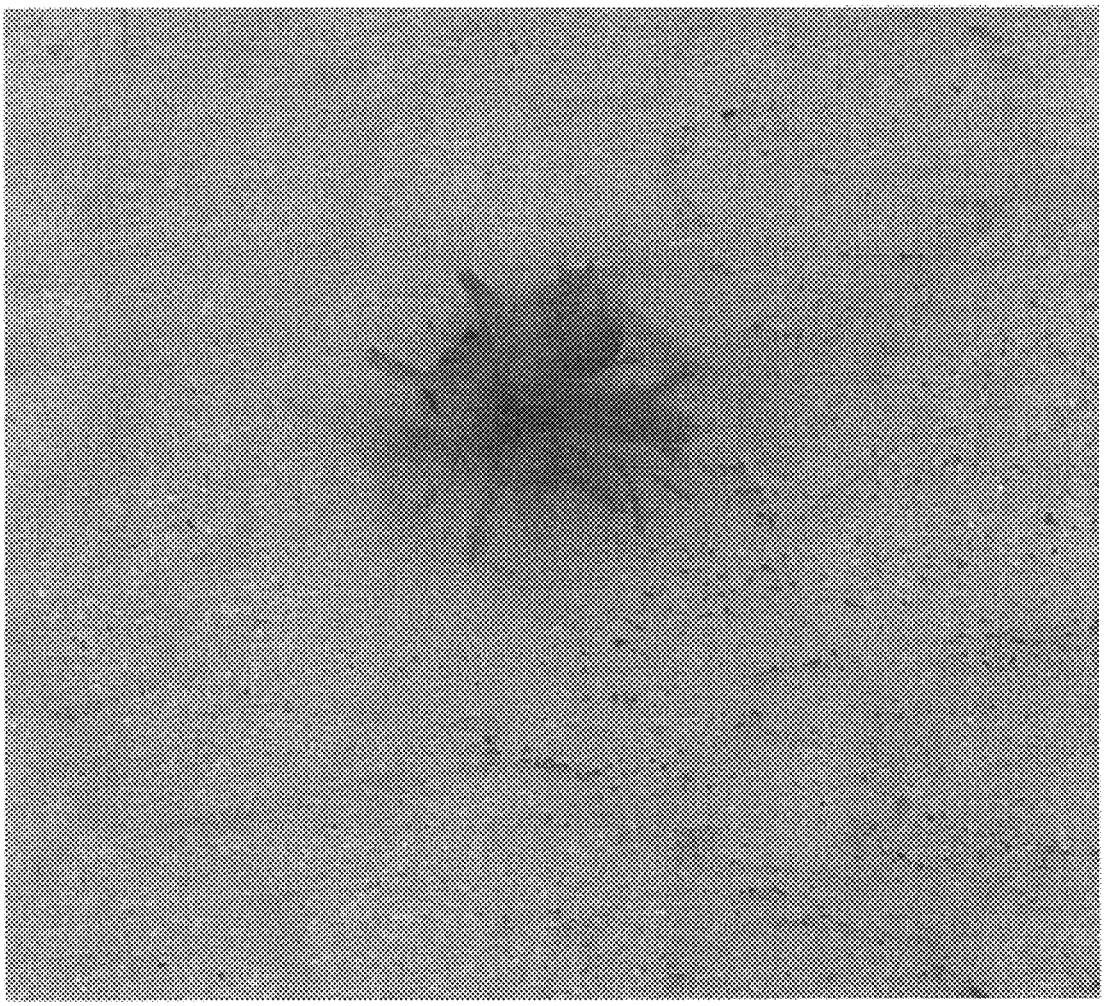
FIG. 2 shows a close-up of a yellow inflorescence of 'Dansolwind' at the age of 10 weeks.

The new *Solidago* cultivar 'Dansolwind' has not been observed under all possible environmental conditions. The phenotype of the new cultivar may vary significantly with variations in environment such as temperature, light intensity, and day length without any change in the genotype of the plant.

The aforementioned photographs, together with the following observations, measurements and values describe the new *Solidago* cultivar as grown in the field in Moshav Mishmar Hashiva, Israel, under conditions which closely approximate those generally used in commercial practice. The photographs and descriptions were taken during September of 2004, when the outdoor day temperature averaged 30° C. and the outdoor night temperature averaged 24° C. The plant was grown with fertilization N:P205:K20 in the ratio of 5:3:8. The age of plants described is 10 weeks.

Color references are made to The Royal Horticultural Society Colour Chart (R.H.S.), 2001, except where general colors of ordinary significance are used. Color values were taken under daylight conditions at approximately 12:00 p.m. in Moshav Mishmar Hashiva, Israel.

Classification:
Botanical: *Solidago* sp.
Parentage:
Female or seed parent: Seedling designated '1-Y-1' (unpatented).
Male parent: Unknown.
Propagation:
Type: Tip cutting.
Time and temperature to initiate and develop roots:
*Summer.*—Time: 10 days to initiate roots, 21 days for a potted plant. Temperature: Night 25° C., Day 35° C.
*Winter.*—Time: 14 days to initiate roots, 25 days for a potted plant. Temperature: Night 18° C., Day 25° C.
Root description: Fibrous Roots.
PLANT:
Crop time: From cuttings, about 10 weeks are required to produce a finished flowering plant.
Plant form: Perennial, goldenrod decorative plant; dense and bushy.
Growth habit: Vigorous.
Height: 70 to 75 cm.
Width (diameter): 27 cm.
Branching habit and arrangement: About 4 to 5 stems, when pinched, rising together from main stem base.
Cold tolerance: Hardy in moderate climate, approximately to 5° C.
Stems:
*Number of stems.*—About 4 to 5 stems, when pinched.
*Length.*—75 cm.
*Width (diameter).*—28–30 cm.
*Internode length.*—4.5–5.0 cm.
*Strength.*—Sturdy.
*Texture.*—Pubescent.
Foliage:
*Quantity.*—About 20 leaves per stem.
*Length.*—8.0 cm.
*Width.*—1.5 cm.
*Overall shape.*—Lanceolate.
*Shape at apex.*—Acute.
*Shape at base.*—Acute.
*Texture.*—Smooth.
*Margin.*—Toothed.
*Color of mature leaf.*—Upper surface: Green, RHS 137C. Lower surface: Green, RHS 137D.
*Color of immature leaf.*—Upper surface: Green, RHS 137D. Lower surface: Yellow-green, RHS 146D.
Venation:
*Pattern.*—Observed, extending from leaf surface. Midrib with secondary veins.
*Color.*—Green, RHS 138B.
Petioles:
*Length.*—2 mm.
*Diameter.*—3 mm.
*Color.*—Yellow-green, RHS 144B.
Inflorescence:
*Type and habit.*—Free-flowing, upward-facing and elongated panicles. Ray and disc florets arranged acropetally on a capitulum.
*Quantity of inflorescences per plant.*—Couple of hundred.
*Fragrance.*—Yes, very faint pleasant smell.
*Flowering response.*—Under natural conditions, plants flower in late summer. At other times of year, flower initiation and development can be induced under (long day) conditions. Response time is 10 weeks.
*Post-production longevity.*—Cut inflorescences maintain for about 10–15 days with no fading. On the plant, inflorescences maintain for about 2–3 weeks.
*Inflorescence diameter.*—3 mm.
*Inflorescence depth (height).*—4 mm.
*Panicle length.*—20 cm.
*Panicle diameter.*—5 cm.
*Disc diameter.*—2 mm.
Buds:
*Length.*—4 mm.
*Diameter.*—1 mm.
*Shape.*—Ellipsoid.
*Rate of opening.*—About 4 to 5 days.
*Color.*—Green, RHS: 144C, below, and yellow, RHS: 13A, above.
Ray florets:
*Number of rays per inflorescence.*—1 row of petals.
*Number of inflorescence per row.*—About 13 to 15 in one row.
*Length.*—3.5 mm.
*Width.*—0.2 mm.
*Overall shape.*—Oblong.
*Shape at apex.*—Rounded.
*Shape at base.*—Wedge shaped.
*Margin.*—Entire.
*Texture.*—Smooth.
*Aspect.*—60° from vertical.
*Color (upper surface).*—Yellow group, RHS 13A.
*Color (under surface).*—Yellow group, RHS 13A.
Disc florets:
*Number of discs per inflorescence.*—About 4 to 6.
*Length.*—2 mm.
*Diameter.*—1 mm.
*Overall shape.*—Spoon shaped.
*Shape at apex.*—Blunt.
*Shape at base.*—Pointed.
*Color (mature).*—Yellow, RHS 13A.
*Color (immature).*—Yellow, RHS 13A.
Involucoral brachts:
*Number per inflorescence.*—About 6 to 8.
*Shape.*—Oblong.
*Shape at apex.*—Rounded.
*Texture.*—Pubescent.
*Color (upper surface).*—Yellow-green, RHS 144A.
*Color (under surface).*—Yellow-green, RHS 144B.
Peduncles:
*Length.*—1 cm.
*Strength.*—Sturdy.

*Angle.*—About 80° degrees to the stem.
*Texture.*—Puberulent.
*Color.*—Yellow-green, RHS N144 D.

Reproductive organs:

Androecium:

*Location.*—On disc florets only.
*Anthers.*—Number: 4 to 6. Size: 1 mm.
*Pollen.*—Amount: Abundant. Color: Yellow, RHS 13A.

Gynoecium:

*Location.*—On ray and disc florets only.
*Pistils.*—Number: 6 to 10. Size: 1 mm. Color: Yellow, RHS 138B.

Seeds:

*Quantity.*—6 to 10.
*Size.*—1 mm.
*Color.*—Greyish-brown, RHS 199C.

Fruit:

*Quantity.*—about 6 to 10.
*Size.*—About 0.5 mm.
*Color.*—Greyish-brown, RHS 199C.

Disease resistance/susceptibility: No information is currently available.

I claim:

1. A new and distinct *Solidago* plant named 'Dansolwind', substantially as illustrated and described herein.

* * * * *